US011000301B1

(12) United States Patent
Rocha-Singh

(10) Patent No.: US 11,000,301 B1
(45) Date of Patent: May 11, 2021

(54) SYSTEMS AND METHODS FOR CAPTURING AND REMOVING VASCULAR DEBRIS

(71) Applicant: Krishna Rocha-Singh, Springfield, IL (US)

(72) Inventor: Krishna Rocha-Singh, Springfield, IL (US)

(*) Notice: Subject to any disclaimer, the term of this patent is extended or adjusted under 35 U.S.C. 154(b) by 0 days.

(21) Appl. No.: 16/845,852

(22) Filed: Apr. 10, 2020

(51) Int. Cl.
*A61B 17/221* (2006.01)
*A61B 17/22* (2006.01)

(52) U.S. Cl.
CPC .... *A61B 17/221* (2013.01); *A61B 2017/2212* (2013.01); *A61B 2017/22049* (2013.01)

(58) Field of Classification Search
CPC ............ A61B 17/221; A61B 17/22031; A61B 2017/22049; A61B 2017/2212; A61B 2017/22035; A61B 2017/22038; A61B 5/6858; A61F 2/013; A61F 2/01; A61F 2/0105; A61F 2/012; A61F 2/011; A61F 2/014; A61F 2002/016; A61F 2002/018
See application file for complete search history.

(56) References Cited

U.S. PATENT DOCUMENTS

| | | | |
|---|---|---|---|
| 6,616,679 B1 | 9/2003 | Khosravi et al. | |
| 7,494,485 B2 | 2/2009 | Beck et al. | |
| 7,879,062 B2 | 2/2011 | Galdonik et al. | |
| 8,052,713 B2 | 11/2011 | Khosravi et al. | |
| 8,617,201 B2 | 12/2013 | Hopkins et al. | |
| 8,728,113 B2 | 5/2014 | Bates | |
| 9,283,066 B2 | 3/2016 | Hopkins et al. | |
| 9,351,749 B2* | 5/2016 | Brady | A61B 17/221 |
| 2005/0085847 A1* | 4/2005 | Galdonik | A61F 2/01 606/200 |
| 2005/0101987 A1* | 5/2005 | Salahieh | A61F 2/013 606/200 |
| 2005/0234501 A1* | 10/2005 | Barone | A61F 2/01 606/200 |
| 2008/0147110 A1 | 6/2008 | Wijeratne | |
| 2008/0234722 A1* | 9/2008 | Bonnette | A61F 2/013 606/200 |
| 2009/0326575 A1* | 12/2009 | Galdonik | A61F 2/013 606/200 |
| 2010/0087850 A1* | 4/2010 | Razack | A61B 17/221 606/200 |

(Continued)

*Primary Examiner* — Jocelin C Tanner
(74) *Attorney, Agent, or Firm* — Eversheds Sutherland (US) LLP; Christopher C. Bolten; Albert K. Heng

(57) ABSTRACT

Distal protection devices ("DPDs") and methods of use thereof for capturing and removing vascular debris are provided. The DPD may include a catheter having a distal region sized and shaped to be advanced in a target vessel of the patient. The distal region of the catheter may include a filter basket and fibrous filter disposed thereon, the fibrous filter upstream of the filter basket. The fibrous filter and the filter basket may both transition between a collapsed delivery state and an expanded deployed state. For example, the fibrous filter may be made of a frame coupled to a plurality of fibers, and may exhibit a helical shape in its expanded state such that the plurality of fibers capture and store vascular debris within the blood vessel. The filter basket may capture any vascular debris not captured by the fibrous filter, and may be collapsed and removed from the patient while retaining the vascular debris.

21 Claims, 9 Drawing Sheets

(56) References Cited

U.S. PATENT DOCUMENTS

| | | |
|---|---|---|
| 2013/0006296 A1 | 1/2013 | McGuckin, Jr. et al. |
| 2013/0053882 A1* | 2/2013 | Hocking .............. A61B 17/221 |
| | | 606/200 |
| 2014/0371782 A1* | 12/2014 | Galdonik ............. A61B 17/221 |
| | | 606/200 |
| 2017/0035445 A1* | 2/2017 | Nguyen ......... A61B 17/320758 |

* cited by examiner

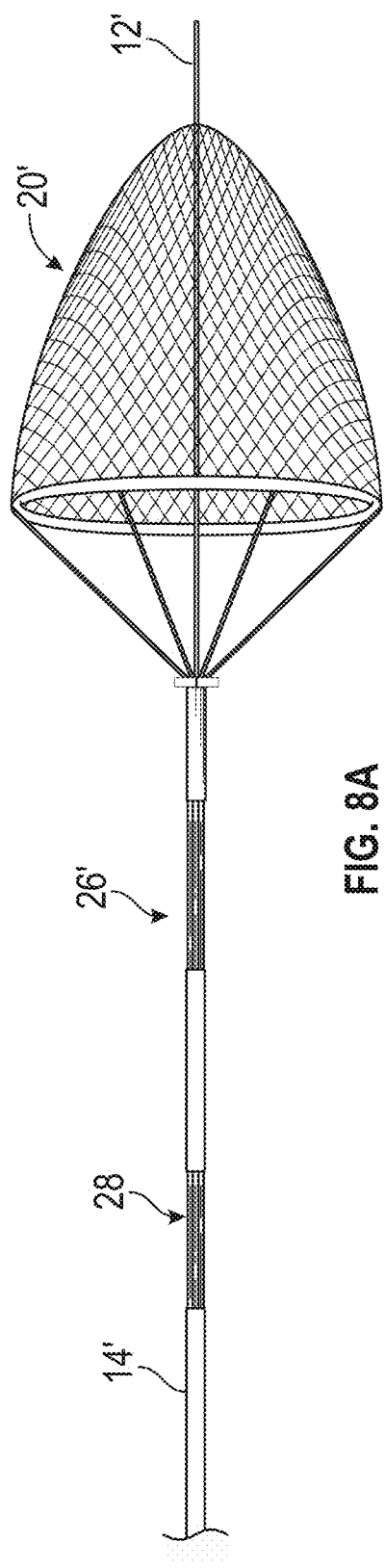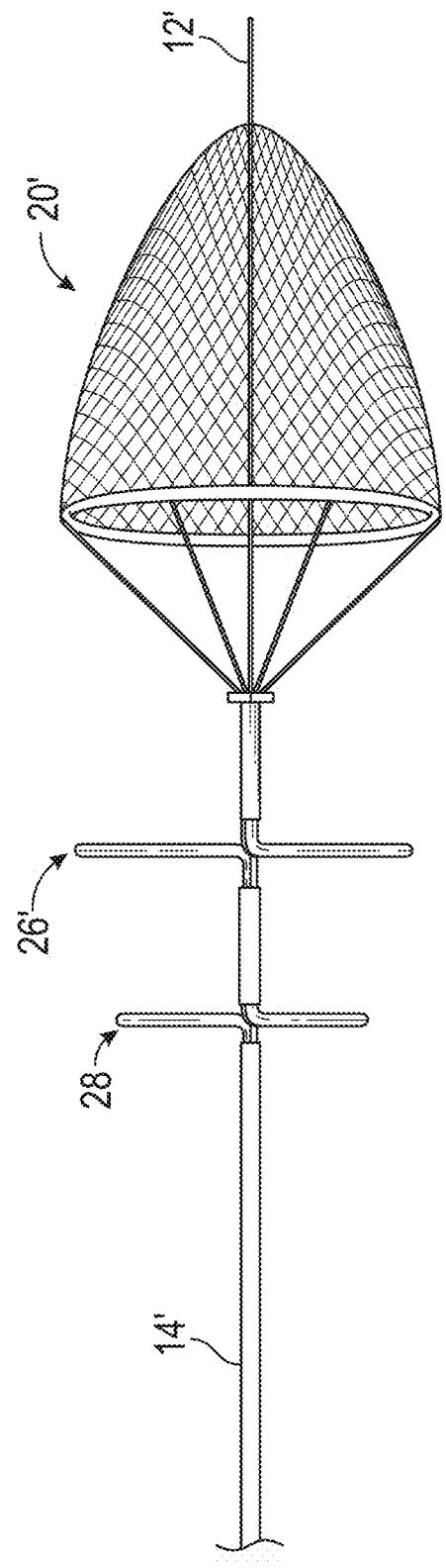

SYSTEMS AND METHODS FOR CAPTURING AND REMOVING VASCULAR DEBRIS

FIELD OF THE INVENTION

This application relates generally to systems and methods for capturing and removing vascular debris during percutaneous interventions.

BACKGROUND

Distal protection devices ("DPDs") are used to capture and remove atherosclerotic and thrombotic debris that dislodges during percutaneous interventions, e.g., percutaneous transluminal angioplasty, stenting, atherectomy, etc. Embolization of this debris may result in procedural complications and poor patient outcomes. Commercially available DPDs are available to protect end-organ parenchyma including the brain, myocardium, kidney and infrapopliteal/pedal vasculature. These DPDs have specific design features that reflect the vascular anatomy in which they are deployed/retrieved and the characteristics of the embolic debris (e.g., particulate size, quantity) they capture. Widely used DPDs include the SpiderFX™ Embolic Protection Device (available by Medtronic, Dublin, Ireland) and the Emboshield NAV6™ Embolic Protection Device (available by Abbott Laboratories, Chicago, Ill.). These commercially available DPDs all employ a filter system comprised of a conical-shaped colander contained within a Nitinol frame, attached or tethered to a steerable guidewire. The colander portion of the DPDs may include ultrathin polymer materials with numerous apertures of varying quantities, diameters and patterns, which serves to filter the blood. However, these DPDs require deployment and retrieval methods of varying complexity. Other DPDs such as those disclosed in U.S. 2008/0147110 to Wijeratne, are designed to improve navigation through tortuous vessels, but suffer from the same potential operational issues.

A known drawback of these filter DPD designs is the propensity for embolized debris to occlude blood flow through the distal most segment of the basket apertures, as shown in FIG. 1, resulting in a "slow flow/no flow" condition. "Slow flow/no flow" results when a static column of blood occurs above the occluded filter basket, thereby preventing perfusion of the distal vasculature, resulting in the inability to visualize the distal vascular bed and its possible ischemia. This is an emergency situation that may require the premature recapture and retrieval of the DPD, thereby interrupting the interventional procedure and releasing embolic debris contained in the static column of blood into the distal parenchyma. Depending on the organ at risk, this may result in a cerebrovascular accident ("CVA"), transient ischemic attack ("TIA"), myocardial infarction ("MI"), renal infarction, or acute limb ischemia and occlusion of small arteries in the foot resulting in ischemia and tissue necrosis (also known as "trash foot").

In addition, DPDs such as those disclosed in U.S. 2013/0006296 to McGuckin, which includes first and second expandable struts having different dimensions when expanded to deploy filter materials, may fail to capture vascular debris and further may release embolic debris during the removal and recapture process.

It would therefore be desirable to provide an improved DPD that prevents accumulation of a substantial amount of atheroembolic debris in the distal most portion of the DPD, thereby minimizing the possibility of a "slow flow-no flow" state within the arterial treatment segment and minimizing the loss of captured embolic material during the DPD retrieval process.

SUMMARY OF THE INVENTION

In accordance with the principles of the present invention, distal protection device systems and methods are provided for capturing and removing vascular debris. For example, the system may include a catheter having a distal region structured to be advanced into a blood vessel and a filter basket coupled to the distal region of the catheter that may transition between a collapsed delivery state and an expanded deployed state. The filter basket captures vascular debris in the blood vessel in the filter basket's expanded deployed state. For example, the filter basket may include a wire frame coupled to a mesh. The wire frame may be formed of a memory shape metal, and may be coupled to the distal region of the catheter via a plurality of Nitinol threads or plurality of fibers. Moreover, the mesh may have a conical shape in the filter basket's expanded deployed state and/or the mesh may be formed by a latticework of capillary fibers.

In addition, the system may include a fibrous filter coupled to the distal region of the catheter upstream of the filter basket that may transition between a collapsed delivery state and an expanded deployed state. The fibrous filter includes a plurality of fibers coupled to a frame that may exhibit a helical shape in the fibrous filter's expanded deployed state such that the plurality of fibers capture vascular debris in the blood vessel. For example, the frame of the fibrous filter may include first and second wires that form the helical shape in the fibrous filter's expanded deployed state. Additionally, the plurality of fibers of the fibrous filter may be formed of a thermoplastic polymer. Moreover, the plurality of fibers of the fibrous filter may extend radially away from a longitudinal axis of the catheter in the fibrous filter's expanded deployed state, and may extend along the longitudinal axis of the catheter in the fibrous filter's collapsed delivery state. The fibrous filter may exhibit a ring shape in its expanded deployed state.

The outer surface of the plurality of fibers may include a plurality of grooves extending along a longitudinal axis of the plurality of fibers, such that the plurality of grooves capture and store vascular debris. In addition, the catheter may have a lumen sized and shaped to receive a guidewire. Accordingly, movement of the catheter relative to the guidewire while the filter basket remains stationary may cause the fibrous filter to transition between the fibrous filter's collapsed delivery state and the fibrous filter's expanded deployed state.

In accordance with another aspect of the present invention, the system further may include a second fibrous filter coupled to the distal region of the catheter upstream of the fibrous filter. The first fibrous filter may include a first diameter in its expanded deployed state, and the second fibrous filter may include a second diameter in its expanded deployed state, such that the second diameter is smaller than the first diameter. For example, the first diameter may be sized to contact an inner wall of a target vessel in the fibrous filter's expanded deployed state, and/or the second diameter may be sized to be less than 50% of a diameter of an inner wall of a target vessel in the second fibrous filter's expanded deployed state. Moreover, the system may include a sheath sized and shaped to be slidably disposed over the fibrous filter in the fibrous filter's collapsed delivery state. Accordingly, the sheath may receive at least a portion of the filter basket to facilitate transition of the filter basket from the filter basket's expanded deployed state to the filter basket's collapsed delivery state.

Methods of using the distal protection devices of the present invention also are provided. For example, the method may include advancing the sheath having the distal region of the catheter disposed therein to the target vessel of the patient; retracting the sheath to expose the filter basket and the fibrous filter, the filter basket self-expanding within the target vessel; transitioning the fibrous filter from its collapsed delivery state to its expanded deployed state within the target vessel; capturing vascular debris via the fibrous filter and the filter basket; transitioning the fibrous filter from its expanded deployed state to its collapsed delivery state; advancing the sheath over the fibrous filter and at least partially over the filter basket to transition the filter basket from its expanded deployed state to its collapsed delivery state; and removing the sheath and the distal region of the catheter from the target vessel.

BRIEF DESCRIPTION OF THE DRAWINGS

FIGS. 8A-8E illustrate the exemplary steps for capturing and removing vascular debris using the DPD of FIG. 7 in accordance with the principles of the present invention.

DETAILED DESCRIPTION OF THE INVENTION

In accordance with the principles of the present invention, systems and methods are provided for capturing and removing vascular debris. For example, the system includes a distal protection device ("DPD") structured to capture vascular debris while preventing accumulation of a substantial amount of atheroembolic debris in the distal most portion of the DPD, thereby minimizing the possibility of a "slow flow-no flow" state within the arterial treatment segment. In addition, the DPD is structured to retain embolic debris captured therein during the removal and recapture process of the DPD from the patient.

Figure 1:
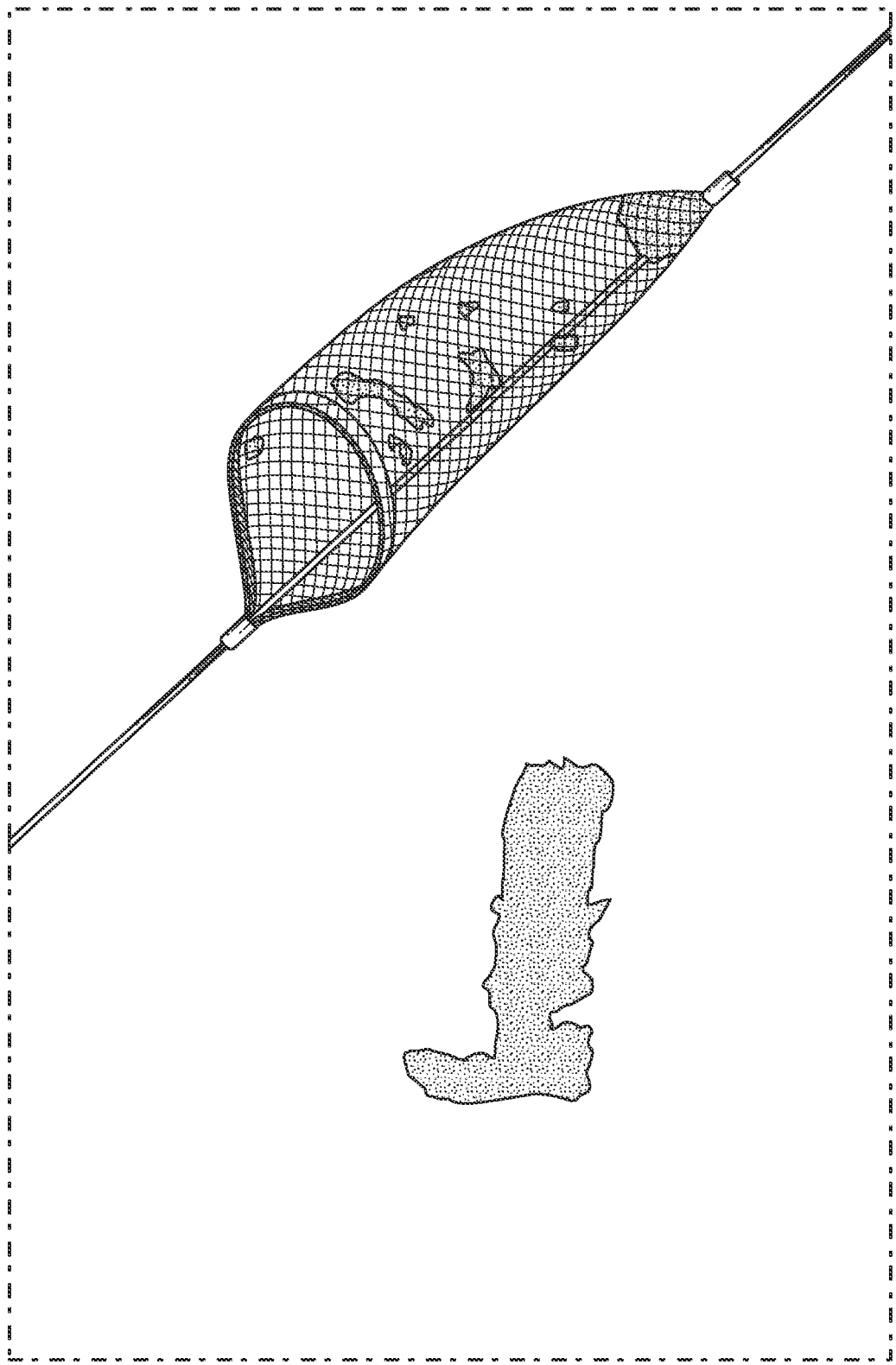
FIG. 1 illustrates embolized debris removed from an occluded filter basket of a commercially available DPD, which prevented perfusion of the distal vasculature, requiring the removal of the DPD.
Figure 2:
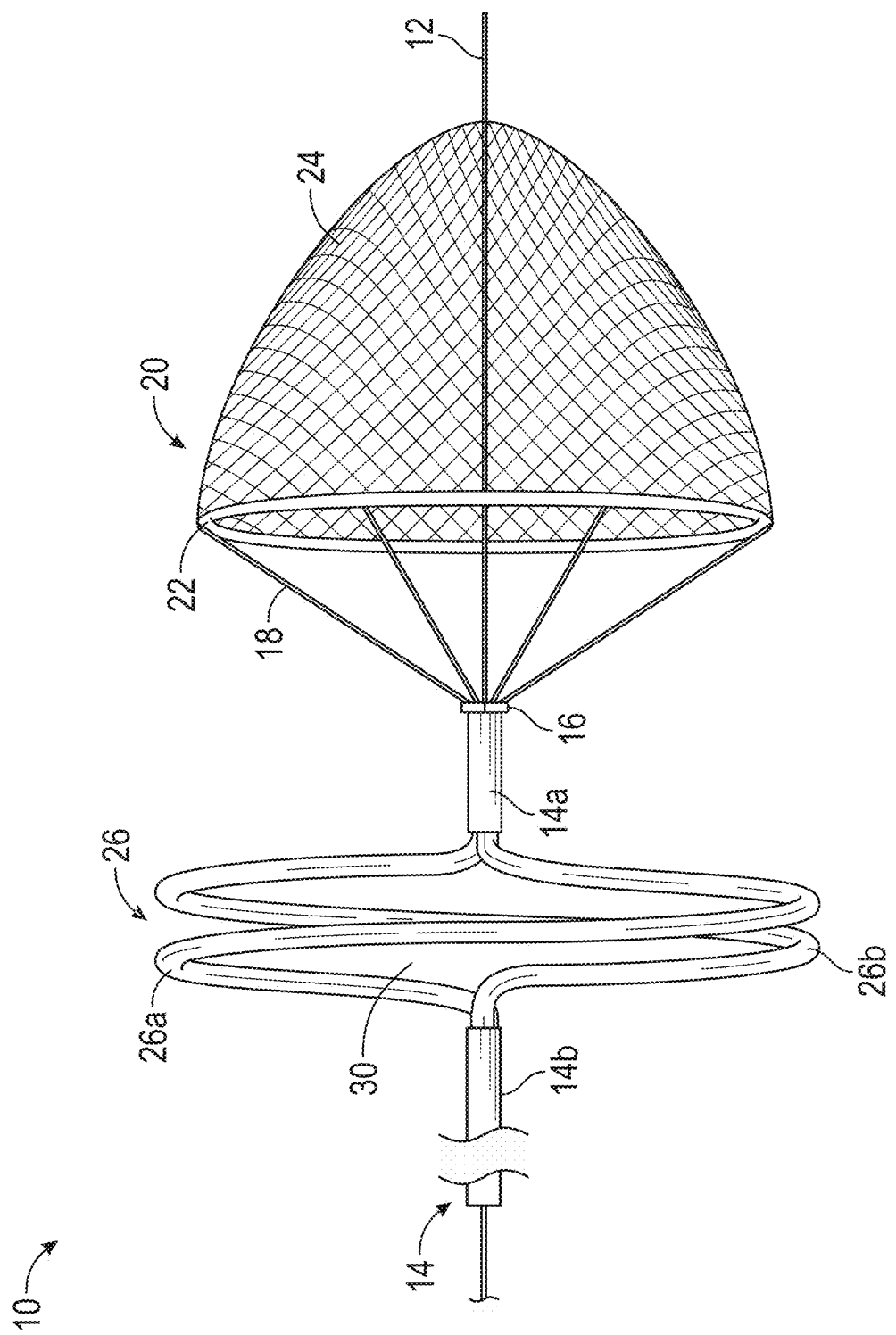
FIG. 2 illustrates an exemplary DPD constructed in accordance with the principles of the present invention.

Referring now to FIG. 2, an exemplary DPD constructed in accordance with the principles of the present invention is provided. DPD 10 may include a hypotube, e.g., catheter 14, having a proximal end that remains external to the patient's vasculature for maneuvering by the physician, a distal region sized and shaped to be positioned within a target site of the patient's vasculature, and a lumen extending therebetween, the lumen sized and shaped to receive an intravascular device, e.g., guidewire 12. Accordingly, catheter 14 may have a length sufficient such that the distal region of catheter 14 is disposed at the target site of the patient's vasculature. As shown in FIG. 2, DPD 10 further may include filter basket 20 and fibrous filter 26 disposed on the distal region of catheter 14, fibrous filter 26 positioned upstream of filter basket 20. Thus, as shown in FIG. 2, distal end 16 of catheter 14 may be coupled to filter basket 20, and a portion of catheter 14 proximal to distal end 16 may be divided into two segments 14a and 14b separated by fibrous filter 26 for transitioning fibrous filter 26 between a collapsed delivery state and an expanded deployed state as described in further detail below.

Filter basket 20 may include wire frame 22, e.g., a shape memory metal such as Nitinol, and porous mesh 24 coupled to wire frame 22. Wire frame 22 is flexible and may self-expand from a collapsed delivery state, e.g., within a delivery sheath, to an expanded deployed state within the patient's vasculature. In the expanded state, wire frame 22 may have a diameter that is close to or the same as the diameter of the target vessel. Alternatively, wire frame 22 may have a diameter that is a predetermined percentage of the target vessel diameter. Porous mesh 24 has a plurality of pores sized to permit blood to flow therethrough, while capturing vascular debris. Thus, as blood flows through porous mesh 24, porous mesh 24 expands and captures vascular debris therein. In accordance with one aspect of the present invention, porous mesh 24 may be made of a latticework of capillary fibers as described in further detail below. In its expanded state, porous mesh 24 may have, e.g., a conical, spiral, or disk shape. As will be understood by a person having ordinary skill in the art, filter basket 20 may be any commercially available filter basket including, e.g., SpiderFX™ Embolic Protection Device (available by Medtronic, Dublin, Ireland) or Emboshield NAV6™ Embolic Protection Device (available by Abbott Laboratories, Chicago, Ill.), and may have a longitudinal length ranging from 0.25 to 1.20 inches depending on the size of the patient's target vasculature and the underlying procedure and debris to be collected.

As shown in FIG. 2, filter basket 20 may be coupled to distal end 16 of catheter 14 via wire frame 22 and one or more connectors 18, e.g., a plurality of Nitinol threads or plurality of capillary fibers as described in further detail below. Accordingly, a delivery sheath may be advanced over one or more connectors 18 to facilitate retrieval of filter basket 20 by causing wire frame 22 to at least partially transition from the expanded deployed state to a partially or wholly collapsed delivery/retrieval state. As the delivery sheath is advanced over one or more connector 18 in a controlled manner, wire frame 22 collapses in a manner that prevents or reduces escape of vascular debris from within mesh 20. Upon collapse of filter basket 20 via the delivery sheath, DPD 10 may be safely removed from the patient's body.

Fibrous filter 26 may include a flexible frame and plurality of fibers 30 coupled to the frame. The frame of fibrous filter 26 may be made of, e.g., a pair of Nitinol wires 26a, 26b, that are transitionable between a collapsed delivery state where the wires 26a, 26b are parallel to the longitudinal axis of catheter 14 and have a first longitudinal length, and an expanded deployed state where wires 26a, 26b exhibit a helical shape about the longitudinal axis of catheter 14 and having a second longitudinal length significantly less than the first longitudinal length. For example, fibrous filter 26 may have a flat, disk-shape in its expanded deployed configuration as shown in FIG. 2. Moreover, in its expanded state, fibrous filter 26 may have a diameter close to or equal to the diameter of the vessel. Alternatively, in its expanded state, fibrous filter 26 may have a diameter that is a predetermined percentage of the target vessel diameter, e.g., 50% of the diameter of the vessel.

Both ends of fibrous filter 26 remain coupled to catheter 14 so that fibrous filter 26 may transition between the collapsed delivery state and the expanded deployed state upon movement of catheter 14 relative to, e.g., guidewire 12 and/or filter basket 20. For example, one end of fibrous filter 26 is coupled to distal component 14a of catheter 14 having distal end 16 coupled to filter basket 20, and the other opposite end of fibrous filter 26 is coupled to proximal component 14b of catheter 14. Thus, relative movement between the proximal and distal components 14b and 14a of catheter 14 will transition fibrous filter 26 between the collapsed delivery state and the expanded deployed state. As will be understood by a person having ordinary skill in the art, the frame of fibrous filter 26 may include less than or more than two flexible wires, e.g., one, three, four or more wires.

Figure 3:
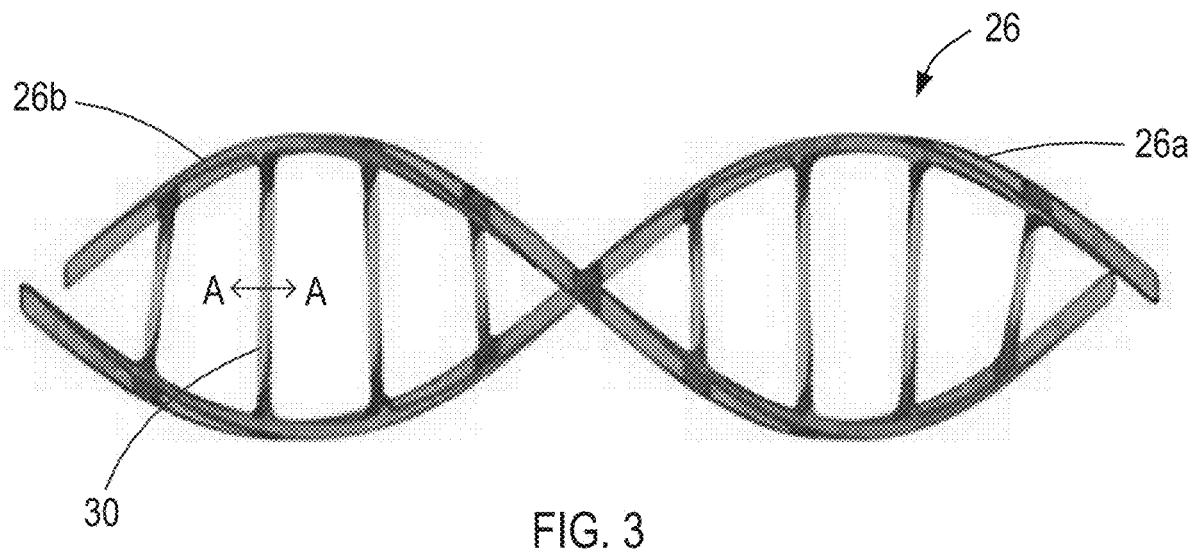
FIG. 3 is an illustrative example of the components of an exemplary fibrous filter having a plurality of fibers in accordance with the principles of the present invention.

As fibrous filter 26 expands, plurality of fibers 30 coupled thereto transitions from a collapsed delivery state where plurality of fibers 30 are parallel to the longitudinal axis of catheter 14 to an expanded deployed state where plurality of fibers 30 extend radially away from the longitudinal axis of catheter 14, thereby forming a disk-like filter for capturing vascular debris. Wires 26a, 26b of the frame of fibrous filter 26 and plurality of fibers 30 may have a structure similar to a helical DNA structure as shown in FIG. 3, such that plurality of fibers 30 are disposed longitudinally along the length of wires 26a, 26b, and extend between wires 26a, 26b. Moreover, the ends of wires 26a, 26b are coupled to catheter 14. Accordingly, in the collapsed delivery state, plurality of fibers 30 may be folded such that they are parallel to the longitudinal axis of catheter 14.

Figure 4:
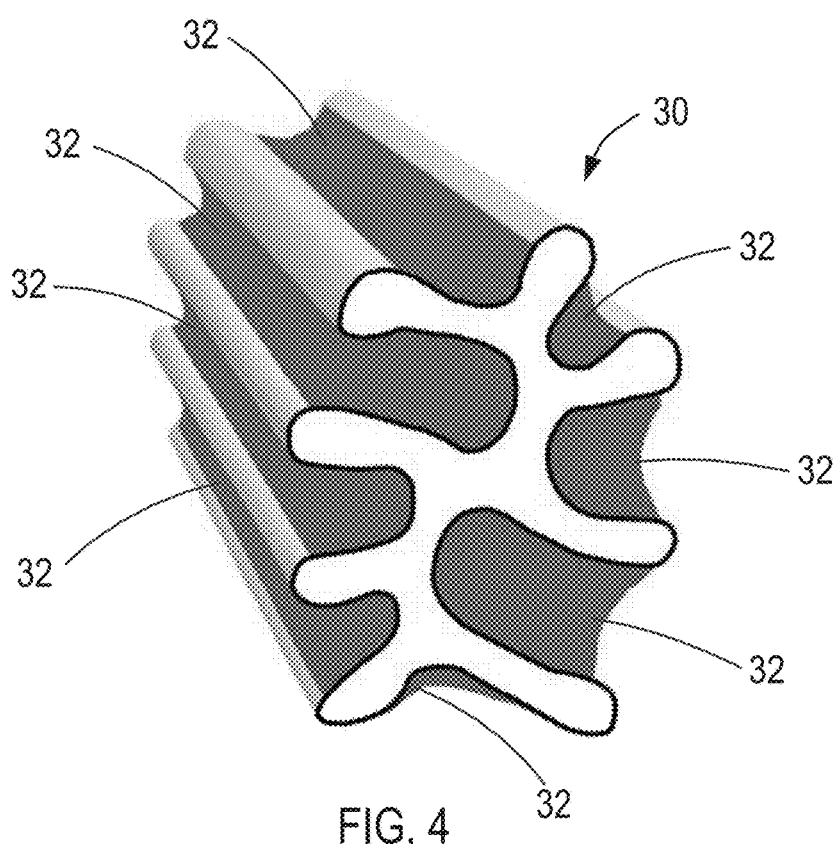
FIG. 4 is a cross-sectional view of an exemplary capillary fiber of a fibrous filter constructed in accordance with the principles of the present invention.

Plurality of fibers 30 may be formed of various thermoplastic polymer materials, e.g., polyethylene terephthalate ("PET") or nylon. Each of the fibers of plurality of fibers 30 may be a capillary fiber having plurality of grooves 32 extending along the longitudinal axis of the capillary fiber in a circumferential pattern on the outer surface of the capillary fiber as shown in FIG. 4, which is a cross-sectional view along line A-A of FIG. 3. FIG. 4 illustrates a 25 µm diameter capillary fiber. The grooves of plurality of grooves 32 may be of various shapes and sizes, such that plurality of grooves 32 capture and store vascular debris therein as blood flows past plurality of fibers 30 of fibrous filter 26. For example, plurality of fibers 30 may be made of 4DG™ (made available by Fiber Innovation Technology, Inc., Johnson City, Tenn.), and may have a structure such as that described in U.S. Pat. No. 7,879,062 to Galdonik, the entire contents of which are incorporated herein by reference. Moreover, as described above, one or more connectors 18 and/or porous mesh 24 also may be formed of similar capillary fibers to improve capture of vascular debris.

Figure 5:
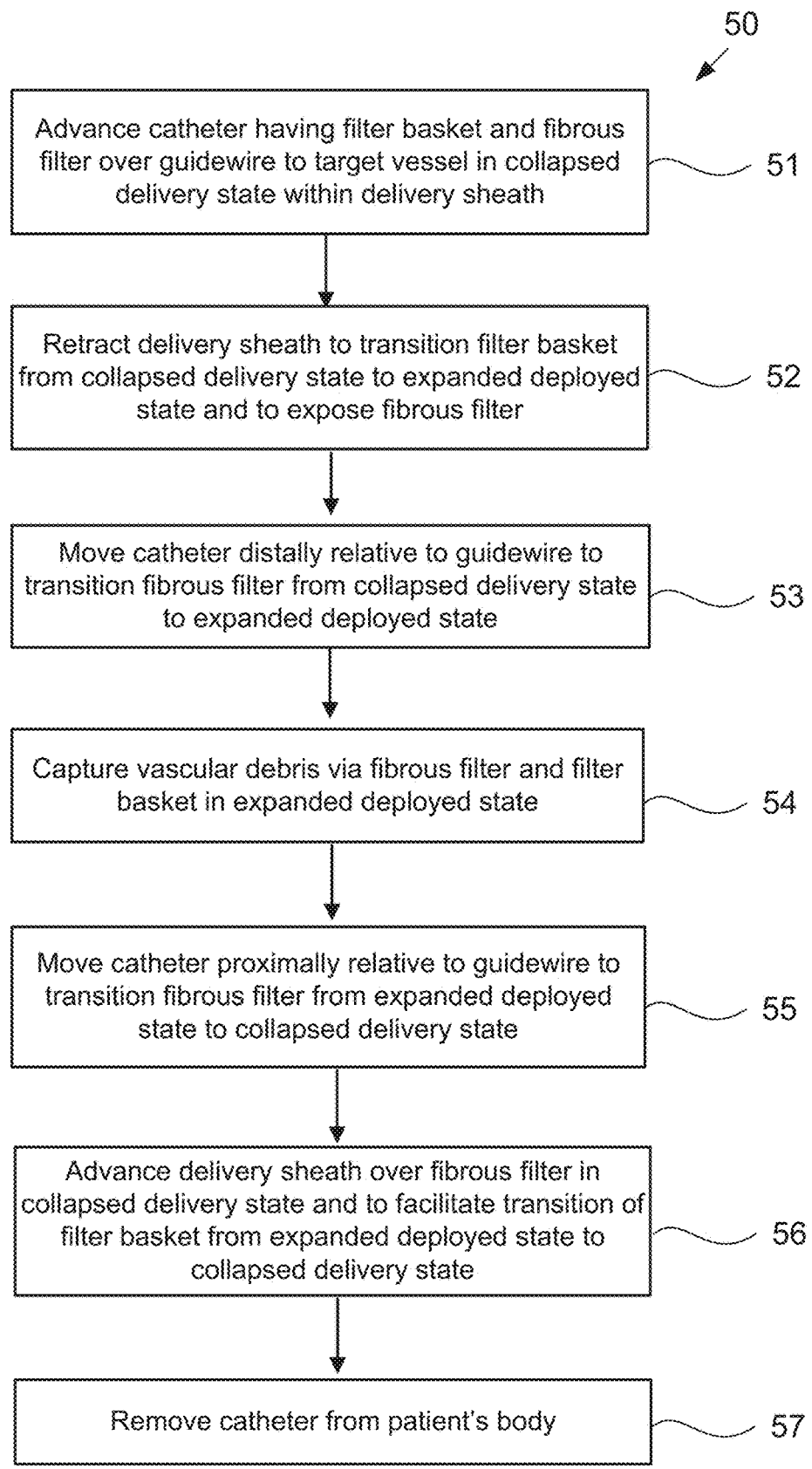
FIG. 5 is a flow chart showing the exemplary steps for capturing and removing vascular debris in accordance with the principles of the present invention.
Figure 6A:
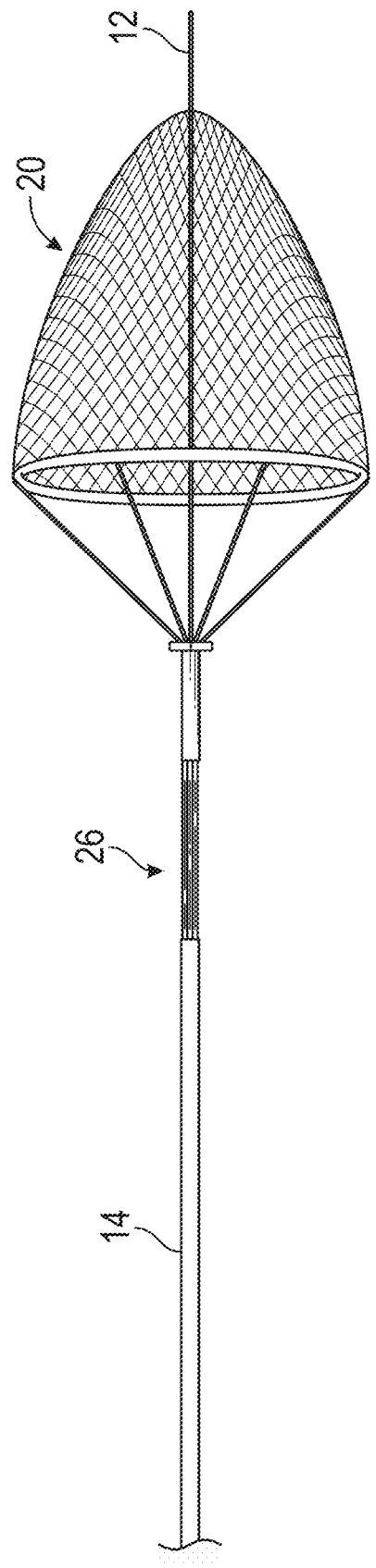
FIGS. 6A-6E illustrate the exemplary steps for capturing and removing vascular debris using the DPD of FIG. 2 in accordance with the principles of the present invention.
Figure 6B:
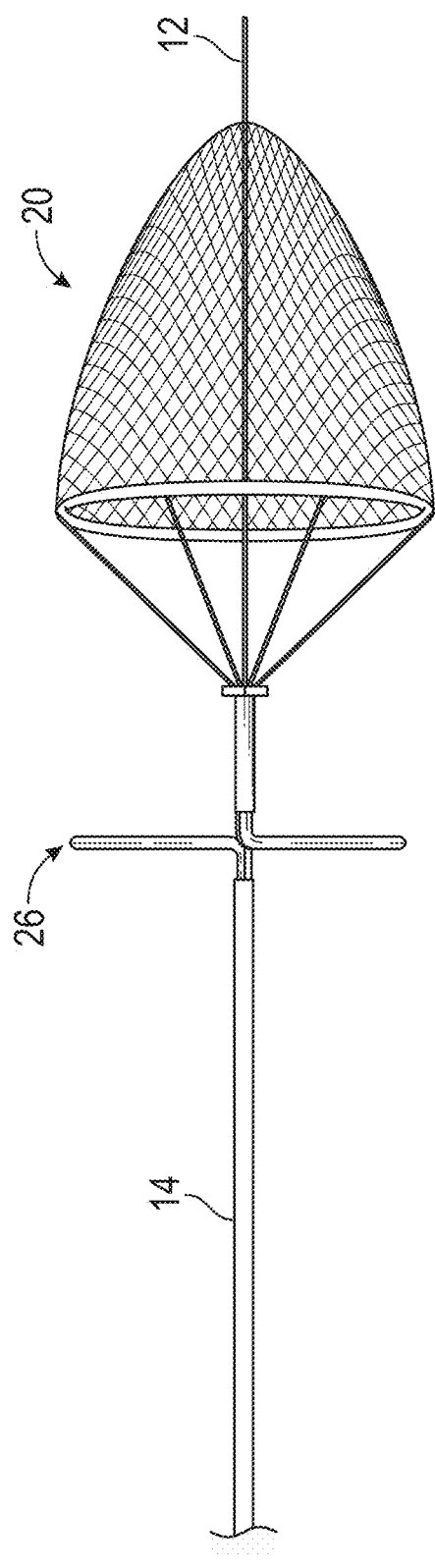

Referring now to FIG. 5, a flow chart showing the steps of exemplary method 50 for capturing and removing vascular debris using, e.g., DPD 10 of FIG. 2, in accordance with the principles of the present invention is provided. Some of the steps of method 50 may further be elaborated by referring to FIGS. 6A to 6E. At step 51, the distal region of catheter 14 having filter basket 20 and fibrous filter 26 in a collapsed delivery state within delivery sheath 60 are advanced over guidewire 12 to a target vessel. At step 52, delivery sheath 60 is retracted to transition filter basket 20 from the collapsed delivery state to an expanded deployed state within the vessel, and to expose fibrous filter 26 in its collapsed delivery state within the vessel, as shown in FIG. 6A. At step 53, catheter 14 is moved distally relative to guidewire 12 and/or filter basket 20, to thereby transition fibrous filter 26 from its collapsed delivery state to its expanded deployed state as shown in FIG. 6B. As shown in FIG. 6B, fibrous filter 26 has a thin, disk-like shape in its expanded deployed state, thereby forming a disk-shape filter of plurality of fibers 30 of fibrous filter 26.

Figure 6C:
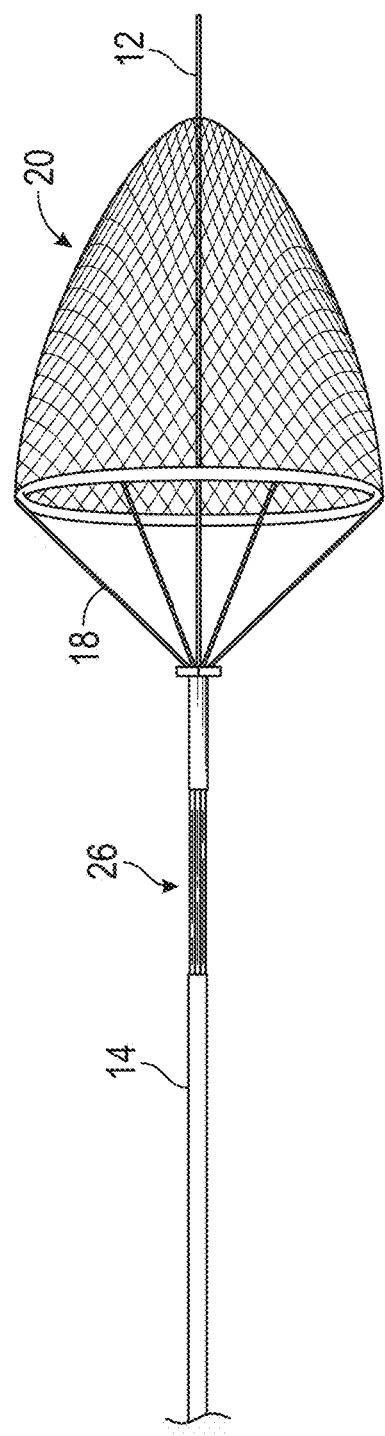
Figure 6D:
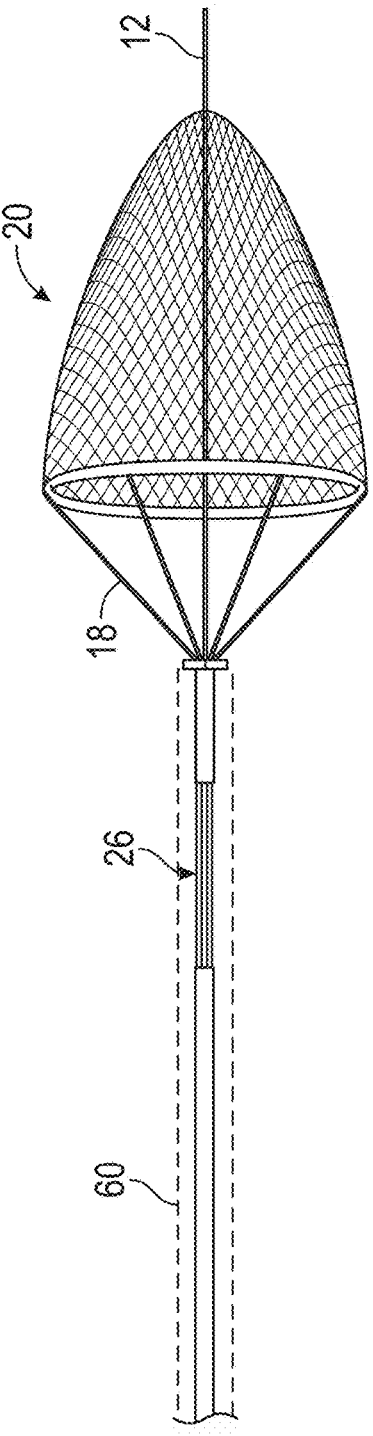
Figure 6E:
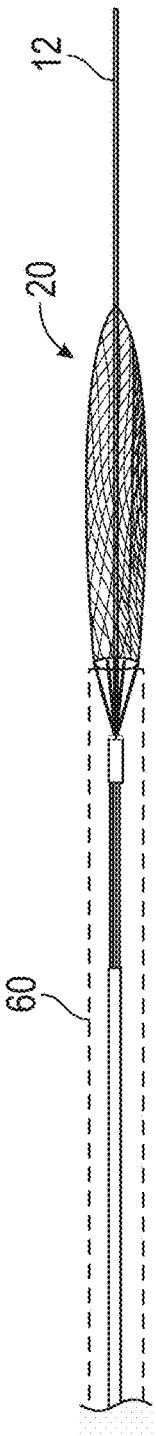

At step 54, deployed fibrous filter 26 captures and stores most, if not all, of the vascular debris in the blood flowing past fibrous filter 26, and porous mesh 24 of filter basket 26 expands and captures any vascular debris that may have been missed by fibrous filter 26. Upon completion of the underlying procedure, when DPD 10 needs to be removed, at step 55 catheter 14 is moved proximally relative to guidewire 12 and/or filter basket 20, to thereby transition fibrous filter 26 from its expanded deployed state to its collapsed delivery state as shown in FIG. 6C, while plurality of fibers 30 retain the captured vascular debris embedded within the plurality of grooves therein. At step 56, delivery sheath 60 is advanced over catheter 14 and over fibrous filter 26 in its collapsed delivery state as shown in FIG. 6D. During step 56, delivery sheath 60 is continually advanced over catheter 14 such that delivery sheath 60 contacts and is advanced over one or more connectors 18 coupled to filter basket 20, thereby facilitating transition of filter basket 20 from its expanded deployed state to its collapsed delivery state, as shown in FIG. 6E. Filter basket 20 is collapsed in a controlled manner such that little or no vascular debris captured by the porous mesh of filter basket 20 escapes during the removal/retrieval process.

As shown in FIG. 6E, at least a portion of filter basket 20 may be disposed within delivery sheath 60, for removal from the patient. Alternatively, the entirety of filter basket 20 may be received within delivery sheath 60 in its collapsed delivery state. At step 57, DPD 10 and delivery sheath 60 may be removed from the patient's body.

Figure 7:
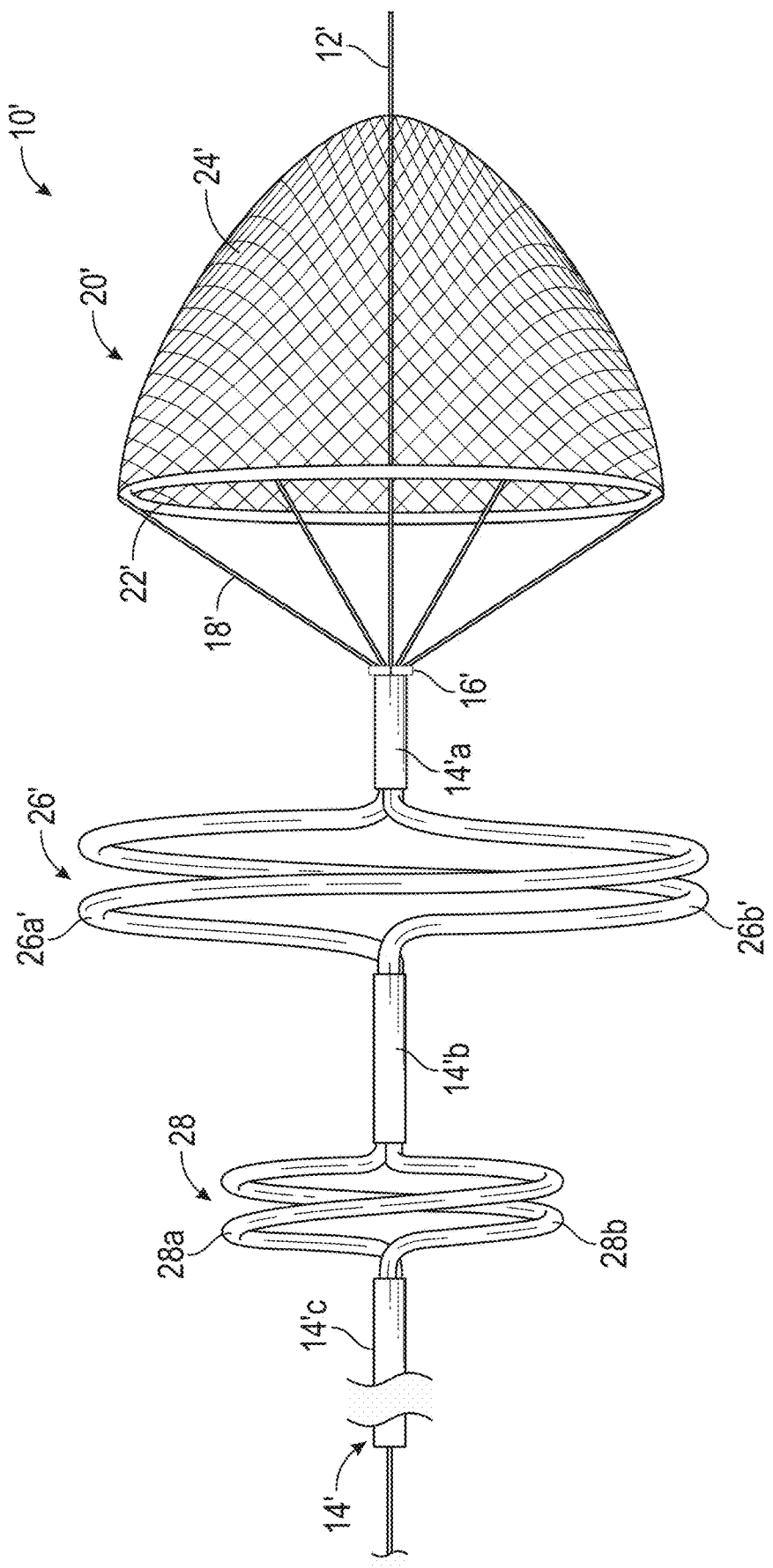
FIG. 7 illustrates an alternate exemplary DPD constructed in accordance with the principles of the present invention.
Figure 8C:
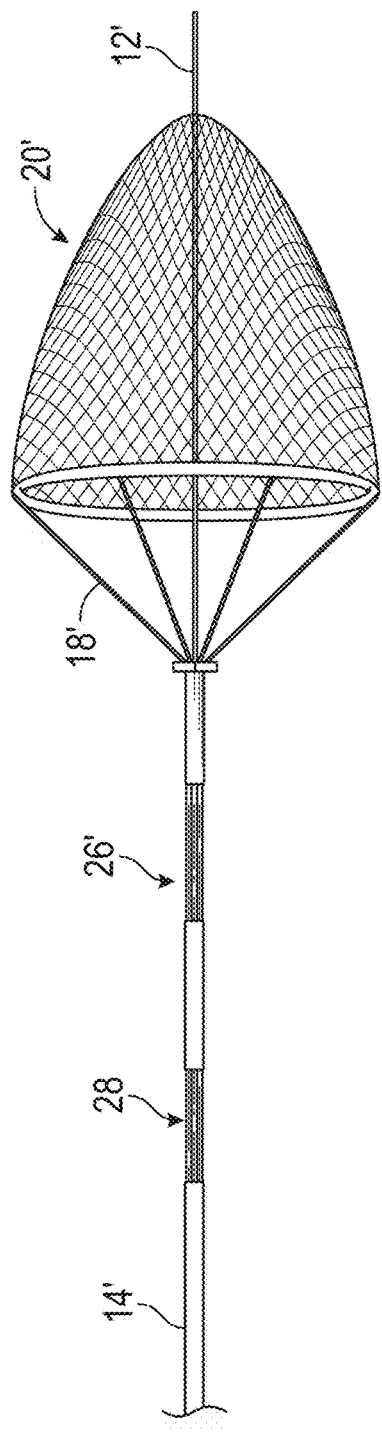
Figure 8D:
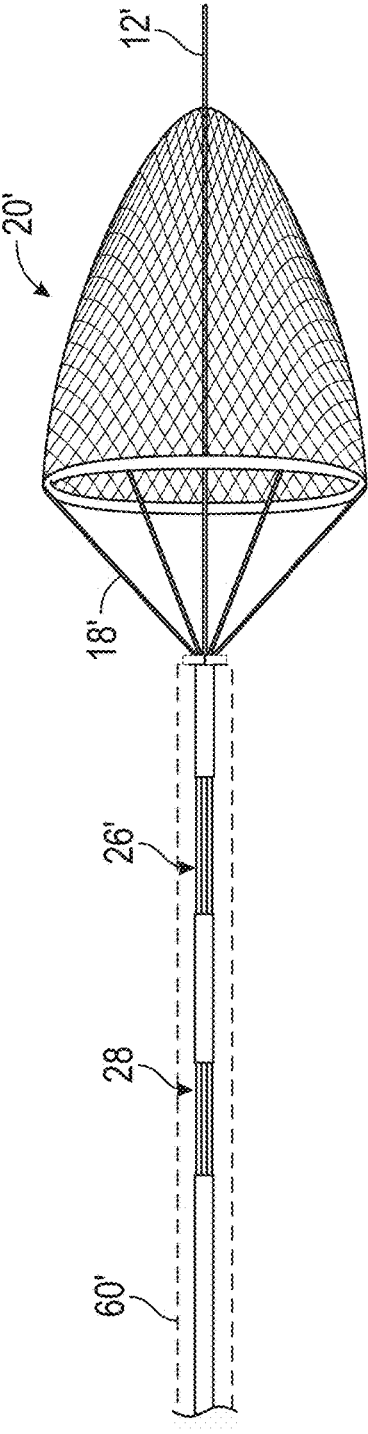
Figure 8E:
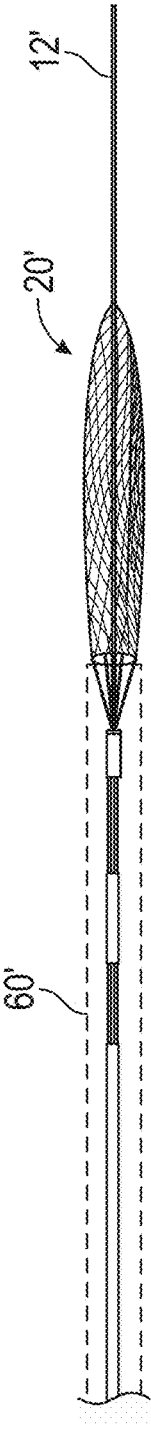

Referring now to FIG. 7, another exemplary DPD constructed in accordance with the principles of the present invention is provided. DPD 10' may be constructed similar to DPD 10 of FIG. 2, with similar components represented by like-primed reference numerals. For example, catheter 14', filter basket 20', and first fibrous filter 26' of FIG. 7 correspond with catheter 14, filter basket 20, and fibrous filter 26 of FIG. 2. DPD 10' of FIG. 7 differs from DPD 10 of FIG. 2 in that DPD 10' includes second fibrous filter 28 disposed on catheter 14' upstream of fibrous filter 26'. For example, second fibrous filter 28 may be formed of two wires 28a and 28b coupled to a plurality of fibers extending therebetween. Accordingly, catheter 14' may be divided into distal component 14a', intermediate component 14b', and proximal component 14c', such that the ends of second fibrous filter 28 may be coupled to proximal component 14c' and intermediate component 14b' of catheter 14', and the end of first fibrous filter 26' may be coupled to intermediate component 14b' and distal component 14a' of catheter 14' as shown in FIG. 7. Thus, relative movement between the proximal and intermediate components 14c' and 14b' of catheter 14' will transition second fibrous filter 28 between the collapsed delivery state and the expanded deployed state, and relative movement between the intermediate and distal components 14b' and 14a' of catheter 14' will transition first fibrous filter 26' between the collapsed delivery state and the expanded deployed state.

Second fibrous filter 28 may be constructed similar to fibrous filter 26 of FIG. 2. Preferably, second fibrous filter 28 has a diameter in its expanded state that is smaller than the diameter of fibrous filter 26' in its expanded state. For example, fibrous filter 26' may have an expanded diameter that is close to or equal to the diameter of the target vessel; whereas, second fibrous filter 28 may have an expanded diameter that is a predetermined percentage less than the diameter of the target vessel, e.g., 40%, 50%, 60%, 70%, 80% of the diameter of the target vessel. As will be understood by a person having ordinary skill in the art, the expanded diameter of second fibrous filter 28 may be any percentage of the target vessel diameter within, e.g., 30-99%, and DPD 10 may include more than two fibrous filters of various diameters to effectively capture vascular debris.

While various illustrative embodiments of the invention are described above, it will be apparent to one skilled in the art that various changes and modifications may be made therein without departing from the invention. For example, a DPD constructed in accordance with the principles of the present invention may include more than two fibrous filter baskets with or without a distal filter basket depending on the underlying procedure and vascular debris to be collected. The appended claims are intended to cover all such changes and modifications that fall within the true scope of the invention.

What is claimed:

1. A system for capturing and removing vascular debris, the system comprising:
    a catheter comprising a distal region configured to be advanced into a blood vessel;
    a filter basket coupled to the distal region of the catheter and configured to transition between a collapsed delivery state and an expanded deployed state, the filter basket configured to capture vascular debris in the blood vessel in the filter basket's expanded deployed state; and
    a fibrous filter coupled to the distal region of the catheter upstream of the filter basket, the fibrous filter configured to transition between a collapsed delivery state and an expanded deployed state, the fibrous filter comprising a plurality of fibers coupled to a frame, the frame configured to exhibit a helical shape in the fibrous filter's expanded deployed state such that the plurality of fibers capture vascular debris in the blood vessel.

2. The system of claim 1, wherein the filter basket comprises a wire frame coupled to a mesh.

3. The system of claim 2, wherein the wire frame comprises a memory shape metal.

4. The system of claim 2, wherein the wire frame is coupled to the distal region of the catheter via a plurality of Nitinol threads or plurality of fibers.

5. The system of claim 2, wherein the mesh comprises a conical shape in the filter basket's expanded deployed state.

6. The system of claim 2, wherein the mesh comprises a latticework of capillary fibers.

7. The system of claim 1, wherein the frame of the fibrous filter comprises first and second wires that form the helical shape in the fibrous filter's expanded deployed state.

8. The system of claim 1, wherein the plurality of fibers of the fibrous filter comprise thermoplastic polymer.

9. The system of claim 1, wherein the plurality of fibers of the fibrous filter extend radially away from a longitudinal axis of the catheter in the fibrous filter's expanded deployed state.

10. The system of claim 1, wherein the plurality of fibers of the fibrous filter extend along the longitudinal axis of the catheter in the fibrous filter's collapsed delivery state.

11. The system of claim 1, wherein an outer surface of the plurality of fibers comprises a plurality of grooves extending along a longitudinal axis of the plurality of fibers, the plurality of grooves configured to capture vascular debris.

12. The system of claim 1, wherein the fibrous filter comprises a ring shape in its expanded deployed state.

13. The system of claim 1, wherein the catheter comprises a lumen configured to receive a guidewire.

14. The system of claim 13, wherein movement of the catheter relative to the guidewire while the filter basket remains stationary causes the fibrous filter to transition between the fibrous filter's collapsed delivery state and the fibrous filter's expanded deployed state.

15. The system of claim 1, further comprising a second fibrous filter coupled to the distal region of the catheter upstream of the fibrous filter.

16. The system of claim 15, wherein the fibrous filter comprises a first diameter in its expanded deployed state, and the second fibrous filter comprises a second diameter in its expanded deployed state, the second diameter smaller than the first diameter.

17. The system of claim 16, wherein the first diameter is sized to contact an inner wall of a target vessel in the fibrous filter's expanded deployed state.

18. The system of claim 16, wherein the second diameter is sized to be less than 50% of a diameter of an inner wall of a target vessel in the second fibrous filter's expanded deployed state.

19. The system of claim 1, further comprising a sheath configured to be slidably disposed over the fibrous filter in the fibrous filter's collapsed delivery state.

20. The system of claim 19, wherein the sheath is configured to receive at least a portion of the filter basket to facilitate transition of the filter basket from the filter basket's expanded deployed state to the filter basket's collapsed delivery state.

21. A method for capturing and removing vascular debris, the method comprising:
    advancing a sheath having a distal region of a catheter disposed therein to a target vessel of a patient, the distal region of the catheter comprising a filter basket and a fibrous filter upstream of the filter basket, the fibrous filter comprising a plurality of fibers coupled to a frame;
    retracting the sheath to expose the filter basket and the fibrous filter, the filter basket self-expanding within the target vessel;
    transitioning the fibrous filter from a collapsed delivery state to an expanded deployed state within the target vessel;
    capturing vascular debris via the fibrous filter and the filter basket;
    transitioning the fibrous filter from the expanded deployed state to the collapsed delivery state;
    advancing the sheath over the fibrous filter and at least partially over the filter basket to transition the filter basket from an expanded deployed state to a collapsed delivery state; and
    removing the sheath and the distal region of the catheter from the target vessel.

\* \* \* \* \*